United States Patent [19]

Hundley

[11] Patent Number: 4,855,492

[45] Date of Patent: Aug. 8, 1989

[54] PROCESS FOR PRODUCTION OF AROMATIC POLYCARBOXYLIC ACIDS

[75] Inventor: John G. Hundley, St. Charles, Ill.

[73] Assignee: Amoco Corporation, Chicago, Ill.

[21] Appl. No.: 199,619

[22] Filed: May 27, 1988

[51] Int. Cl.$^4$ ............................................. C07C 51/265
[52] U.S. Cl. ..................................... 562/414; 562/413; 562/416; 562/417
[58] Field of Search ................. 562/414, 413, 416, 417

[56] References Cited

U.S. PATENT DOCUMENTS 4,357,475 11/1980 Hanotier et al. ...................... 562/414
4,560,793 12/1985 Hashizume et al. ................. 562/414

Primary Examiner—Werren B. Lone
Assistant Examiner—Vera C. Clarke
Attorney, Agent, or Firm—Gunar J. Blumberg; William M. Magidson; Ralph C. Medhurst

[57] ABSTRACT

A continuous process for producing a polycarboxylic acid product is disclosed. The process comprises combining a methyl substituted aromatic hydrocarbon, an oxidation catalyst, and an oxygen-containing gaseous stream in a reaction zone to produce a reaction mixture. The oxygen-containing gaseous stream includes noncondensible gases. The reaction mixture in the reaction zone is subjected to a predetermined temperature and pressure for a predetermined residence time to produce an admixture of reactants and reaction products. The reaction products include a vapor phase and a product-containing liquid phase. Heat is removed from the product-containing liquid phase by withdrawing a portion of such liquid stream from the reaction zone and passing such reaction zone-removed portion to a heat-removal/separation zone.

10 Claims, 2 Drawing Sheets

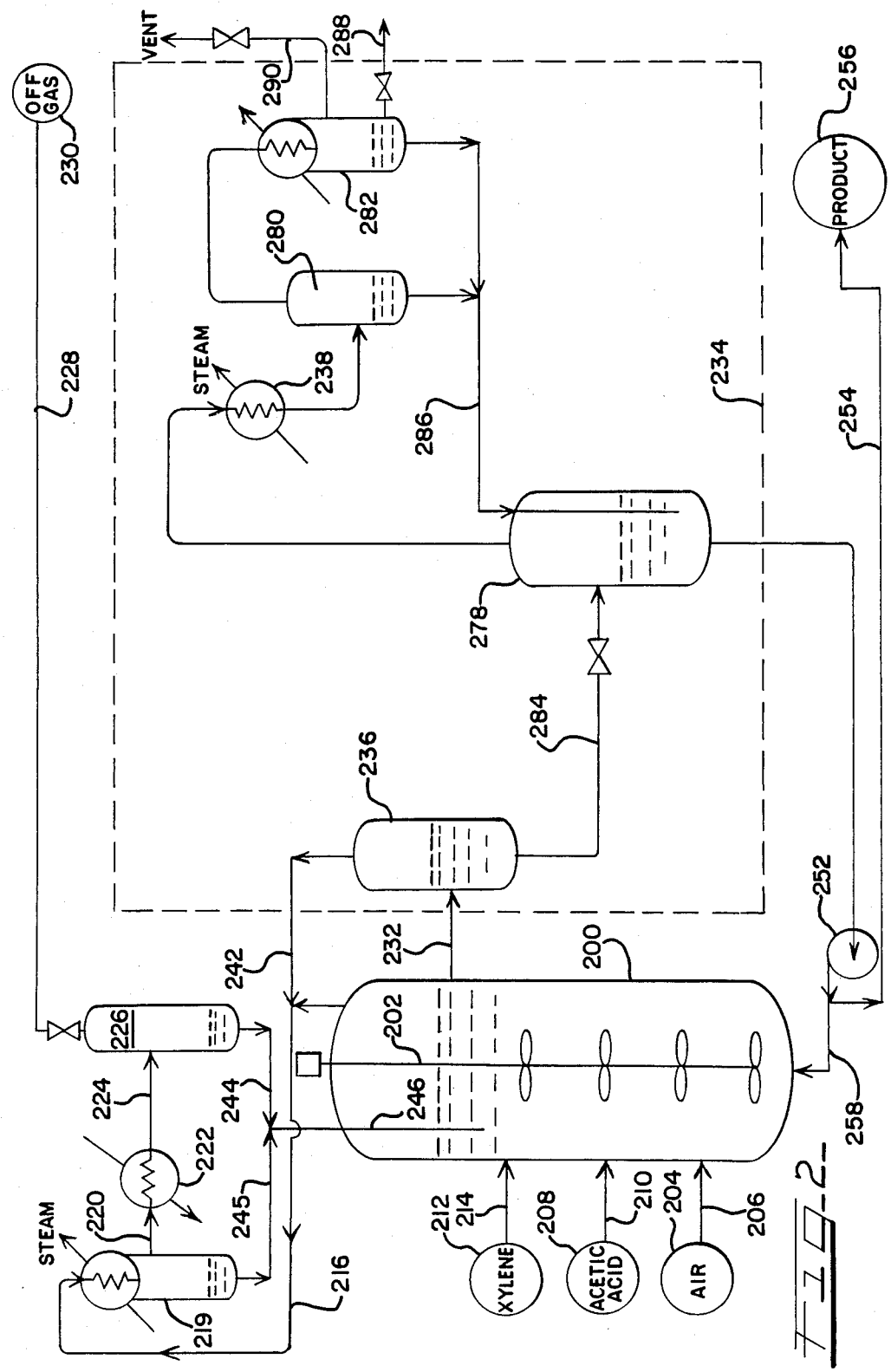
FIG_2

PROCESS FOR PRODUCTION OF AROMATIC POLYCARBOXYLIC ACIDS

Technical Field

The present invention relates to improvements in a process for continuous production of aromatic polycarboxylic acids by oxidation of polymethyl substituted aromatic hydrocarbons.

BACKGROUND OF THE INVENTION

Aromatic polycarboxylic acids are conventionally produced by liquid phase catalytic oxidation of feedstocks containing a polymethyl substituted aromatic hydrocarbon, such as a xylene. Such liquid phase reaction systems are shown in U.S. Pat. Nos. 3,170,768 and 3,092,658, both to Baldwin. Because the chemical conversion of the polymethyl substituted aromatic reactant to the aromatic polycarboxylic acid product is known to be exothermic, reaction solvents are typically employed to dissipate the resultant heat of reaction in a reflux loop. The current practice is to produce the aromatic polycarboxylic acid product in a continuous process or system that includes an oxidation reactor equipped with a reflux system. The reactor contents include water, di or trimethyl substituted hydrocarbon reactants, reaction solvent, and a suitable oxidation catalyst for effecting conversion of the reactants to the desired polycarboxylic acid product. The oxidation reactor is also equipped with means for agitating the reactor contents.

In a conventional continuous oxidation process for producing aromatic dicarboxylic acid from a xylene, excess heat of reaction is typically removed via vaporization of the reaction solvents. More particularly, the solvent vaporization typically takes place in the oxidation reactor; and condensation of the vapors emanating from the reaction admixture typically takes place in a series of heat exchangers included within an overhead system. The heat exchangers, typically physically located above the oxidation reactor, allow condensed solvent to be refluxed to the oxidation reactor by gravity.

In one conventional process, the elevated heat exchangers are utilized to separate the water-containing and reactant-bearing solvent vapors into a water-rich aqueous liquid fraction and a reactant-enrich vapor stream. The water-rich aqueous liquid fraction is then removed from the elevated heat exchangers while the reactant-enriched vapor stream is further processed to recover vaporized reactant and solvent. Removal of the water-rich fraction in this manner reduces the concentration of water in the reactor-contained solvent which, in turn, lowers the concentration of oxidation catalyst that is required to effect the desired conversion reaction.

The above-mentioned overhead system includes steam-generating heat exchangers, water-cooled heat exchangers, gas-liquid separator equipped with means for venting non-condensible gases, and scrubbers. In the steam-generating overheat heat exchangers, which are generally of shell-and-tube construction, condensation of the vaporized reaction solvent takes place on the tube side while useful process steam is generated on the shell side. The water-cooled heat exchangers, typically located down stream of the steam-generating exchangers, are utilized for the purpose of assisting in the condensation of the vaporized solvent before the condensed solvent is returned to the oxidation reactor, generally as reflux. Effluent from the water-cooled exchangers is passed to the gas-liquid separators. Condensed liquid, recovered via the separators, is returned to the oxidation reactor. Residual reactant-bearing solvent vapors as well as non-condensible gases are vented from the separators and passed through the scrubbers which serve to further recover unreacted reactant and solvent from the non-condensible gas-bearing vapors before such vapors are vented. In certain situations, such vapors are passed through energy-recovery devices, such as an expansion turbine, before venting.

Many conventional oxidation reactors were originally designed to operate at a predetermined temperature range. For a variety of reasons, including product quality, it has become desirable to reduce the reaction temperature to below the temperature ranges previously utilized for the oxidation reaction.

For example, reduced reaction temperatures tend to reduce undesirable burning losses of the polymethyl aromatic reactant as well as the solvent. Reduced reaction temperatures have also been observed to result in a reduction of undesirable oxidation reaction by-products. Thus, it is desirable to reduce the process temperature range so as to improve product yields and quality while reducing operating costs of the process.

In the conventional polymethyl aromatic oxidation process, lower reaction temperatures require a simultaneous reduction in the reactor operating pressure. However, as the reactor pressure is reduced, vapor velocities in the reactor increase with attendant reduction in reactor liquid phase residence times. Pressure drops in overhead piping and heat exchanges increase as well. Consequently, as the reactor temperatures are lowered in a conventional polymethyl aromatic oxidation process, equipment limitations are encountered which require either a reduction in unit throughput or significant capital expenditures for equipment alterations needed to maintain capacity.

Moreover, as the system total pressure is reduced in a conventional process to achieve the desired lower temperature, the oxygen partial pressure at a given dry basis vent oxygen content is also reduced. This imposes an undesirable limitation on operable oxygen partial pressures.

Lower reaction temperatures in the conventional process also reduce the available temperature differential for generating steam at a useful pressure in the reactor overhead hot condensers.

Accordingly, it would be desirable to provide an improved polymethyl aromatic oxidation process that can be operated at relatively lower process temperatures while obviating, or at least minimizing, the aforementioned difficulties when the conventional aromatic alkyl oxidation process is operated at such relatively lower process temperatures. The present improved process satisfies the foregoing desires.

SUMMARY OF THE INVENTION

The present invention contemplates a continuous process for the production of a polymethyl substituted aromatic polycarboxylic acid product from an aromatic hydrocarbon-containing feedstock which provides for effective heat removal from the reactants while in liquid phase. The process of the present invention, briefly stated, comprises combining a polymethyl substituted aromatic hydrocarbon such as a xylene, an aqueous solvent, an oxidation catalyst, and an oxygen-containing gas in an agitated reaction zone, to produce an agitated reaction mixture a portion of which is treated to remove heat therefrom. The greater the fraction of total heat removed from the reaction zone in this manner, the higher is the reactor operating pressure and the oxygen partial pressure in the reactor at a given dry basis vent oxygen level.

In the reaction zone, the agitated reaction mixture is subjected to a predetermined reaction temperature and pressure for a predetermined time to produce an admixture of reactants and reaction products. The reaction zone is defined by a pressurized reactor that contains a vapor phase and a product-containing liquid phase.

Heat is removed from the product-containing liquid phase by withdrawing a portion of the product-containing liquid phase from the reaction zone and passing such portions, thus removed from the reaction zone, to a heat-removal/separation zone. In this zone, hereinafter referred to as a separation zone for brevity, the reaction zone-removed portion is separated into a product-containing liquid stream and a vapor stream and heat is removed from the product-containing liquid stream.

One benefit derived from utilization of the process of the present invention is that the oxidation reaction temperature can be reduced while maintaining a steam-generating capability for the process that is at least as great as, but generally greater than, that of the conventional aromatic hydrocarbon oxidation process described above.

Another benefit derived from utilization of the process of the present invention is that a reduction in the oxidation reaction temperature does not require increasing the vent-gas oxygen concentration in order to obtain oxygen partial-pressure levels in the reactor necessary to achieve desired oxidation reaction.

These and other benefits derived from utilizing the process of the present invention will be discussed further hereinbelow.

BRIEF DESCRIPTION OF THE DRAWINGS

In the drawings:

FIG. 2 is a schematic representation of yet another system embodying certain other principles of the process of the present invention.

Figure 1:
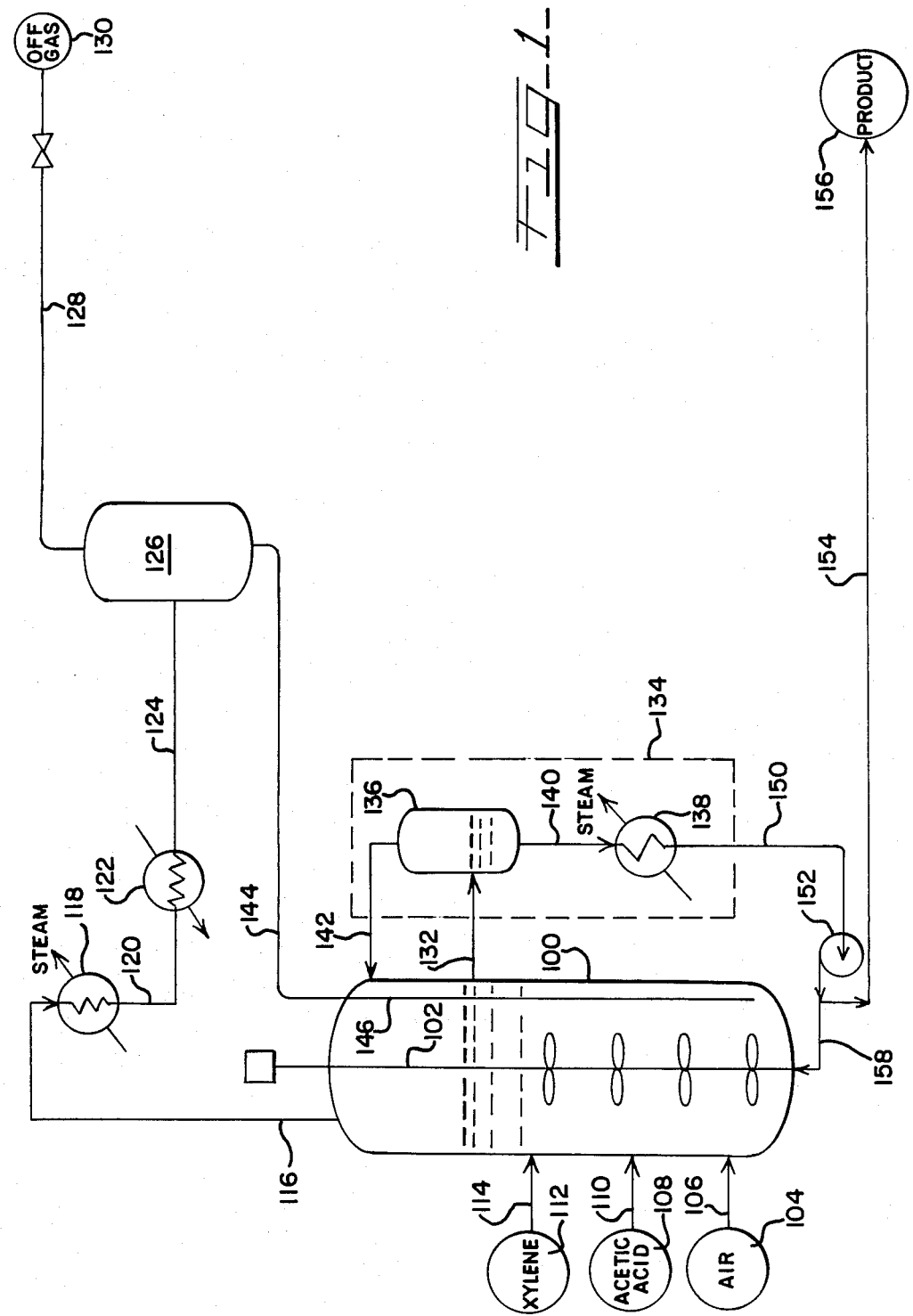
FIG. 1 is a schematic representation of one system embodying certain principles of the process of the present invention.

In the two Figures, parts or components that are the same or similar are referred to by reference numerals having the same last two digits. For example, certain components identified by reference numerals of the 100-series in FIG. 1, which are the same as or similar to certain other components presented in FIG. 2, are identified by reference numerals of the 200-series in FIG. 2.

DETAILED DESCRIPTION OF PREFERRED EMBODIMENTS

While the present invention is susceptible to embodiment in various forms, there are shown in the accompanying drawings and hereinafter described in detail, a number of processes as well as a number of systems embodying the principles of the present invention. The present disclosure, therefore, is to be considered merely as an exemplification of the present invention disclosed herein, without limitation of the specific embodiments illustrated.

Referring to FIG. 1, there is shown a system which embodies the principles of the process of the present invention.

Suitable polymethyl substituted aromatic hydrocarbons useful as reactor feed-mixture components or reactants in the method of the present invention include polymethyl substituted benzenes such as the dimethylbenzenes o-xylene, m-xylene, p-xylene, and the trimethybenzenes such as pseudocumene and mesitylene. The respective aromatic polycarboxylic acid products of these polymethyl substituted aromatic hydrocarbons are the dicarboxylic acids, orthophthalic acid, isophthalic acid, terephthalic acid, and the benzenetricarboxylic acids, such as trimellitic acid and trimesic acid. The method of this invention can be used to produce terephthalic acid, isophthalic acid, and trimellitic acid (1,2,4-benzenetricarboxylic acid). It is particularly well suited for the production of terephthalic acid.

Suitable aqueous solvents useful in practicing the method of this invention are aqueous solutions of aliphatic acids that are readily volatilizable at the reaction temperatures. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caproic acid, and mixtures thereof. Preferably, the volatilizable monocarboxylic aliphatic acid solvent is an aqueous acetic acid solution.

Suitable catalyst systems for present purposes can include any catalyst system conventionally used for liquid-phase oxidation of an aromatic alkyl. A suitable catalyst system, e.g., may include a mixture of cobalt, manganese and bromine compounds or complexes, soluble in the particular volatilizable aqueous solvent employed. A preferred catalyst system is a solution prepared from dry cobalt, selected manganese acetates, and water. A preferred catalyst system may also include a promoter such as aqueous hydrogen bromide.

Reactor feed ingredients, comprising an oxygenated gas, solvent, and reactant, are introduced into a pressurizable oxidation reactor 100 equipped with an agitator 102. The oxygen-containing gas, e.g., air, is provided by an air source 104 and introduced into reactor 100 via a conduit 106. The solvent, e.g., aqueous acetic acid, is provided by solvent source 108 and is introduced into reactor 100 via a conduit 110. The reactant to be oxidized, e.g., p-xylene, is provided by a p-xylene source 112 and is introduced into reactor 100 via a conduit 114. In certain situations, it may be expedient to combine the solvent and reactant into a single feed stream.

The desired oxidation catalyst can be included with either the liquid reactant, or with the solvent. Alternatively, the catalyst can be included with the single feed stream (mentioned above) which is a combination of the liquid reactant and the solvent.

Reactor 100 is pressurized and defines an agitated reaction zone wherein the solvent, the suitable polymethyl substituted aromatic hydrocarbon, the oxidation catalyst and the oxygen-containing gaseous stream are combined to produce an agitated reaction mixture.

The agitated reaction mixture in pressurized reactor 100 is maintained at a predetermined reaction temperature and pressure for a predetermined residence time to produce an admixture of reactants and reaction products. A vapor phase and a product-containing liquid phase are present in the reaction zone.

Reactors for conventional processes utilized to produce an aromatic dicarboxylic acid, typically operate at a temperature range of about 425° to about 435° F. and at a pressure range of 365 to about 385 psia. In contradistinction, a reactor for the present process can operate at a temperature as low as about 350° F. and at a pressure in the range of about 300 to about 400 psia.

Safety considerations mandate that the oxidation process is operated at vent-gas oxygen concentrations of less than about 6 mole percent (dry basis) to avoid the possibility of an explosive vapor composition in the overhead vapor system. Accordingly, oxygen levels of vent gas preferably are set at about 3 to about 5 mole percent oxygen.

In accordance with the system depicted in FIG. 1, a portion of the reactor vapor phase, which possesses sensible and latent heat, exits reactor 100 into a reflux loop via conduit 116, and is introduced into a steam-generating hot condenser 118 by conduit 116. Boiler-feed water is preferably utilized to recover at least some of the latent and sensible heat from the vapor phase, thereby partially condensing the vapor phase and producing useful process steam as well.

The now partially-condensed reactor vapor phase is next introduced via a conduit 120 into a water-cooled cold condenser 122, which further removes some of the latent and sensible heat, to produce a two-phase composition that is transferred via a conduit 124 to a gas-liquid separator 126 from where the liquid phase of the two-phase composition is returned, directly via conduit 144 or indirectly as will be described in greater detail hereinbelow, to the reaction zone.

The gaseous portion of the two-phase composition is conveyed via a valved pipeline 128 to an off-gas site 130 for further processing, as desired. For example, because the off gas typically includes residual vapors of reactant and solvent, as well as non-condensible gases, it may be economically advantageous to recover at least some of the residual reactant and/or solvent vapors before the non-condensible gases are vented.

In addition, heat is removed from the product-containing liquid phase in reactor 100 by withdrawing a portion of the liquid phase from reactor 100 and passing such removed portion via a discharge pipe 132 to a separation zone 134. In FIG. 1, the separation zone 134 comprises a gas-liquid separator 136 and a steam-generating exchanger 138. Accordingly, as is more particularly shown in FIG. 1, the product-containing liquid phase is passed via discharge pipe 132 into separator 136. The product-containing liquid phase, which contains dissolved and entrained gases, is separated in separator 136 into a product-containing liquid stream and a vapor stream. The product-containing liquid stream is passed via a conduit 140 into steam-generating exchanger 138. Because of the limited solubility of the oxidation reaction products in the liquid stream at the conditions in the steam-generating exchanger, it is preferably a non-fouling type, such as a scraped surface exchanger. The vapor stream is returned to the reactor headspace via vapor-return line 142 where it is commingled with the vapor phase that is present in the headspace. The vapor stream, which possesses latent and sensible heat and which includes a small amount of non-condensible gases and condensible materials, combined with the vapor phase in the headspace results in a vapor mixture, a portion of which is passed through the reflux loop, i.e., through the condensers 118 and 122, separated by separator 126 into gaseous and liquid fractions, and the liquid fraction returned to the reaction zone as described hereinabove.

All or a portion of the condensate from separator 126 is returned back to reactor 100 via a reflux line 144 which terminates in a dip tube 146. The refluxed condensate is returned to the relatively lower portion of the reaction zone defined by reactor 100 via dip tube 146. Alternatively, a portion of condensate from separator 126 is returned back to the relatively lower portion of the reaction zone defined by reactor 100 via the separation zone 134, as for example via a conduct not shown in FIG. 1 from separator 126 to separator 136 where condensate is admixed with the product-containing liquid phase.

The remainder of the condensate from separator 126 passes to a waste disposal system or, alternatively, to a solvent recovery and dehydration system not shown. Liquid effluent, which contains the desired oxidation reaction product, exits separator 136 via conduit 140, and then is passed through exchanger 138, for process steam-generating and energy-utilization purposes, as described above. The product-containing stream exiting exchanger 138 is conveyed via a conduit 150 to a transfer pump 152, Pump 152 transfers a portion of the product-containing stream, via a product-transfer line 154, to a product-collection point 156 for product storage or for further processing, as desired. Pump 152 pumps the remainder of the combined stream into the base of the reactor 100 via return line 158.

When the above-described system (FIG. 1) is used to produce isophthalic acid, to the above-mentioned conventional system, it has been calculated, based upon a 4.0 mole percent (dry basis) of oxygen in the vent gas, when the oxidation reaction temperature is about 365° F. and the oxidation reaction total pressure is about 320 to about 370 psia, in reactor 100, that the oxygen partial pressure in reactor 100 is between about 8 and about 10 psi, while a significant amount of the heat of reaction is removed from reactor 100 via steam-generating exchanger 138.

Referring to FIG. 2, air from a source 204, acetic acid from a source 208, and p-xylene from a source 212, are introduced via respective conduits 206, 210, and 214 into an oxidation reactor 200 which contains a suitable oxidation catalyst. The oxidation reactor 200 is pressurizable and is equipped with agitator 202.

The air, the p-xylene, the oxidation catalyst, and the reaction solvent are thus combined in an agitated reaction zone, defined by reactor 200, to produce an agitated reaction mixture. The agitated reaction mixture in the reaction zone is then subjected to a predetermined reaction temperature, preferably in a range of about 350° to about 380° F. and a pressure, preferably in a range of about 320 to about 370 psia, for a predetermined residence time to produce an admixture of reactants and reaction products, all contained within reactor 200. These reaction products include a vapor phase and a product-containing liquid phase.

The vapor phase, which includes vaporized reactant and solvent as well as non-condensible gases, passes upwardly through reactor 200 and is conveyed via a conduit 216 to a steam-generating surface condenser 219. Condenser 219 is able not only to produce useful process stream by recovering latent and sensible heat from this vapor phase stream, but additionally, is able to separate the now partially-condensed reaction vapor phase into liquid and vapor fractions. In particular, the vapor fraction from a surface condenser 219 is passed via a conduit 220 to a water-cooled cold condenser 222, and thence from cold condenser 222 via a conduit 224 to a gas-liquid separator 226, for reasons discussed above in connection with the embodiment shown in FIG. 1. Also as discussed above, off gas is transferred to a site 230 via a valved pipeline 228.

Condensate produced by surface condenser 219 and separator 226 is combined and is returned to reactor 200 by reflux line 244, return line 245, and dip tube 246.

Heat is removed from the product-containing liquid phase within the reaction zone by withdrawing a portion of such liquid phase from the reaction zone, via a discharge pipe 232, and passing such portion to a separation zone 234.

The separation zone 234 depicted in FIG. 2 comprises a gas-liquid separator 236 and a steam-generating condenser 238, and preferably includes a flash vessel 278 operatively interconnecting the gas-liquid separator 236 to the steam-generating condenser 238. The separation zone 234 preferably further includes a vapor-liquid separator 280 and a surface condenser 282, operatively connected between the steam-generating condenser 238 and a flash vessel 278.

In the separation zone 234, the product-containing liquid phase is separated in gas-liquid separator 236 into a product-containing liquid steam and a vapor stream. Such vapor stream contains, in addition to non-condensible gases, amounts of vaporized reactant and solvent. Accordingly, such vapor stream is passed, by vapor-return line 242 to conduit 216, where such vapor is combined with the above-mentioned vapor phase exiting from the reaction zone, and thereafter condensed and separated as described hereinabove.

The product-containing liquid stream produced by separator 236 is passed via a valved conduit 284 to flash vessel 278, which is preferably operated at a temperature in a range of about 325° to 370° F. and a pressure in a range of about 75 to 125 psia.

Thus, in operation, and in accordance with the principles of the present invention, liquid-phase cooling is obtained by flashing a portion of the reaction-mixture liquid to a temperature that is below the reaction temperature, thereby recovering useful energy by passing flashed vapor produced in flash vessel 278 to steam-generating exchanger 238 where such vapor is condensed, and where useful processed steam is generated.

Further in accordance with the principles of the present invention, a major portion of the condensate produced by separator 280 and condenser 282 is refluxed back to flash vessel 278 via reflux line 286. A minor portion of the condensate can be drawn off from the separation zone 234, utilizing a valved draw-off line 288, as desired. A valved vent line 290 can be utilized to vent non-condensible gases from the separation zone 234.

In operation, transfer pump 252 is utilized to transfer a portion of the product-containing liquid stream received from the flash vessel 278. From pump 252, such portion is transferred via a product transfer line 254 to product-collection point 256, for crystallization or other processing of the product-containing liquid stream, as desired. The remainder of the product-containing liquid stream received from flash vessel 278 is returned by pump 252 to reactor 200 via return line 258.

In operation, the system components of the process depicted in FIG. 2 permit a major portion of the non-condensibles to be separated from the reactor effluents by operation of separators 226 and 236. Because such separation is prior in time to flash vaporization in flash vessel 278, a significant amount of useful process steam-generation can be achieved utilizing steam-generating condenser 238.

What has been illustrated and described herein is a novel process for production of an aromatic dicarboxylic acid while recovering useful heat. The process of the present invention has been illustrated and described with reference to several preferred embodiments; however, the present invention is not limited thereto. Alternatives, changes, and modifications of the illustrated embodiments will become apparent to those skilled in the art upon reference to the foregoing description. Accordingly, such alternatives, changes, and modifications are to be considered as forming a part of the present invention insofar as they fall within the spirit and scope of the appended claims.

I claim:

1. A continuous process for producing a polycarboxylic acid product, comprising:
    combining in a reaction zone polymethyl substituted benzene, an oxidation catalyst, an aqueous solvent and an oxygen-containing gas to produce a reaction mixture;
    subjecting the reaction mixture in the reactants and reaction products, including a vapor phase and a product-containing liquid phase;
    removing heat from the product-containing liquid phase by withdrawing a portion of the product-containing liquid phase from the reaction zone and passing said reaction zone-removed portion to a separation zone;
    generating in the separation zone a product-containing liquid stream and a vapor stream;
    cooling the product-containing liquid stream; and
    returning the cooled product-containing liquid stream to the reaction zone.

2. The process in accordance with claim 1 wherein the polymethyl substituted benzene is pxylene and the aqueous solvent is an aqueous solution acetic acid.

3. The process in accordance with claim 1 wherein the vapor stream is returned directly to the reaction zone and is commingled therein with the vapor phase and wherein at least a portion of the vapor phase is condensed to produce a condensate stream.

4. The process in accordance with claim 3 wherein the polymethyl substituted benzene is pxylene and the aqueous solvent is an aqueous solution acetic acid.

5. The process in accordance with claim 1 wherein the vapor stream is commingled with a portion of the vapor phase separately withdrawn from the reaction zone to produce a combined vapor stream, and wherein at least a portion of the combined vapor stream is condensed to produce a condensate stream.

6. The process in accordance with claim 5 wherein the polymethyl substituted benzene is pxylene and the aqueous solvent is an aqueous solution acetic acid.

7. The process in accordance with claim 1 wherein the product-containing stream generated in the separation zone is cooled by flashing to produce second vapor stream and a cooled product-containing stream.

8. The process in accordance with claim 7 wherein the polymethyl substituted benzene is pxylene and the aqueous solvent is an aqueous solution acetic acid.

9. The process in accordance with claim 7 wherein
    at least a portion of the second vapor stream is condensed to produce a condensate stream;
    combining at least a portion of the condensate stream with the cooled product-containing liquid stream to produce a combined stream; and
    returning the combined stream to the reaction zone.

10. The process in accordance with claim 9 wherein the polymethyl substituted benzene is pxylene and the aqueous solvent is an aqueous solution acetic acid.

* * * * *

UNITED STATES PATENT OFFICE
CERTIFICATE OF CORRECTION

Patent No. 4,855,492      Dated August 8, 1989

Inventor(s) John G. Hundley

It is certified that error appears in the above-identified patent and that said Letters Patent is hereby corrected as shown below:

| Col. | Line | |
|---|---|---|
| 8 | 20 | "in the reactants" and should read --in the reaction zone to a predetermined temperature and pressure for a predetermined residence time to produce an admixture of reactants-- |

Signed and Sealed this

Tenth Day of July, 1990

*Attest:*

HARRY F. MANBECK, JR.

*Attesting Officer*      *Commissioner of Patents and Trademarks*